United States Patent [19]

Carlyle et al.

[11] 4,237,126
[45] Dec. 2, 1980

[54] 2β, 16β-BIS-PIPERIDINO-ANDROSTANES

[75] Inventors: Ian C. Carlyle, Hamilton; Thomas Sleigh, Wishaw; David S. Savage, Glasgow, all of Scotland

[73] Assignee: Akzona Incorporated, Asheville, N.C.

[21] Appl. No.: 67,878

[22] Filed: Aug. 20, 1979

[30] Foreign Application Priority Data

Sep. 5, 1978 [GB] United Kingdom ............... 35667/78

[51] Int. Cl.$^3$ ............................................. A61K 31/58
[52] U.S. Cl. .................................. 424/241; 260/239.5
[58] Field of Search ...................... 260/239.5; 424/241

[56] References Cited

U.S. PATENT DOCUMENTS

| | | | |
|---|---|---|---|
| 3,872,091 | 3/1975 | Hewett et al. | 260/239.5 |
| 4,101,545 | 7/1978 | Tuba et al. | 260/239.5 |
| 4,110,326 | 8/1978 | Tuba et al. | 260/239.5 |

FOREIGN PATENT DOCUMENTS

| | | | |
|---|---|---|---|
| 2319370 | 7/1976 | France | 260/239.5 |
| 1138605 | 1/1969 | United Kingdom | 260/397.4 |
| 1454749 | 3/1976 | United Kingdom | 260/239.5 |

OTHER PUBLICATIONS

Journal of Medicinal Chemistry (1973), 16 by Buckett et al.

*Primary Examiner*—Elbert L. Roberts
*Attorney, Agent, or Firm*—Robert H. Falk; Charles A. Wendel; Francis W. Young

[57] ABSTRACT

New and pharmacologically useful pharmaceutically acceptable acid addition salts are disclosed for the 16β-mono-quaternary ammonium derivatives of either the 2β, 16β-bis-piperdino-3-α, 17β-dihydroxy-5α-androstane 3α, 17β-di-lower aliphatic esters of the 2β, 16β-bis-piperidino-3α-hydroxy-5α-androstane-3α-lower aliphatic esters, which salts are surprisingly relatively stable in aqueous solutions, so that they provide stable aqueous injection preparations.

30 Claims, No Drawings

2β, 16β-BIS-PIPERIDINO-ANDROSTANES

BACKGROUND OF THE INVENTION

1. Field of the Invention

The Invention relates to the field of pharmacologically active 2β,16β-bis-piperidino-androstanes, and more specifically, to the use of bis-quaternary ammonium compounds of derivatives of said androstanes as neuromuscular blocking agents.

2. Description of the Prior Art, and Other Information

From British Pat. No. 1,138,605, incorporated herein, (see also U.S. Pat. No. 3,553,212) it is known that certain bis-quaternary ammonium compounds of 2β,16β-bis-piperidino-3α,17β-dihydroxy-5α-androstane-3α,17β-diesters are highly active neuromuscular blocking agents.

A similar observation was made in Journal of Med. Chemistry 16, 1116, 1973, incorporated herein, but besides bis-quaternary ammonium compounds of 2β,16β,bis-piperidino-3α,17β-dihydroxy-5α-androstane-3α,17β-diesters, also 16-mono-quaternary ammonium compounds of these diesters are described to have the same order of potency as the corresponding bis-quaternary compounds.

16-Mono quaternary- as well as 2,16-bis quaternary ammonium compounds of 2β,16β-bis-piperidino-3α-hydroxy-5α-androstane-3α-esters are further known from the British Pat. No. 1,454,749, incorporated herein (see also U.S. Pat. No. 3,872,091).

It has been found that the 16-mono-quaternary ammonium derivatives of the said mono- and diesters in question turned out to be even more interesting compounds than the corresponding bis-quaternary ammonium compounds because of their quicker onset and shorter duration of action, which offer under most surgical conditions pronounced advantages, and because of their lack of cardiovascular side-effects.

However, in contrast to the bis-quaternary compounds, the 16-mono-quaternary ammonium compounds of 2β,16β-bis-piperidino-3α,17β-dihydroxy-5α-androstane 3α,17β-diesters and the corresponding 17β-unsubstituted 3α-mono-esters start to decompose almost immediately when dissolved in water and hence cannot be used in aqueous injection preparations.

Since neuromuscular blocking agents are mainly used in surgical treatments and are administered through injection, it would be a definite advance in the art to possess a stable aqueous injection preparation containing the 16-mono-quaternary ammonium compound of 2β,16β-bis-piperidino-3α,17β-dihydroxy-5α-androstane 3α,17β-diesters or of the corresponding 17β-unsubstituted-3α-mono-esters.

Surprisingly, it has now been found that the pharmaceutically acceptable acid addition salts of the 16β-mono-quaternary ammonium derivatives of either 2β,16β-bis-piperidino-3α,17β-dihydroxy-5α-androstane 3α,17β-di-lower aliphatic esters or 2β,16β-bis-piperidino-3α-hydroxy-5α-androstane-3α-lower aliphatic esters are relatively stable in aqueous solutions to the extent that they can provide stable aqueous injection preparations.

Particularly preferred are the acid addition salts of compounds of the general formula (I):

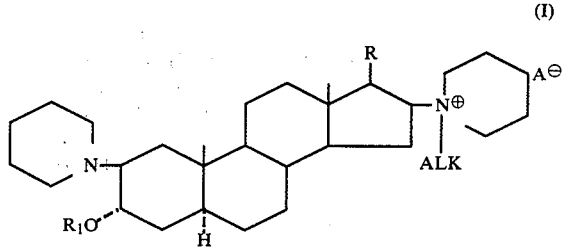

(I)

wherein:
(a) R is hydrogen or the moiety —$OR_2$;
(b) $R_1$ and $R_2$ each represent an unsubstituted acyl group derived from a lower aliphatic carboxylic acid of one to about six carbons;
(c) ALK is an unsubstituted alkyl, alkenyl or alkynyl group of one to four carbon atoms; and
(d) $A^\ominus$ represents a pharmaceutically acceptable organic or inorganic anion.

DESCRIPTION OF THE PREFERRED EMBODIMENTS

The acyl group in the definition of $R_1$ and $R_2$ is derived from lower aliphatic carboxylic acids of from one to about six carbons carbon atoms, for example, acetic acid, propionic acid, butyric acid, pentanoic acid, hexanoic acid, pivalic acid and iso-butyric acid; the acetyl group being a preferred moiety.

Examples of suitable ALK-groups in the compounds of formula I are methyl, ethyl, propyl, butyl, allyl, ethynyl and propargyl. The methyl group is especially preferred.

The anion ($A^\ominus$) used to neutralise the 16-quaternary ammonium cation in compound I may in principle be any pharmaceutically acceptable organic or inorganic anion known to those in the art. Preferred anions are methyl-sulphate, p-toluene-sulphonate and especially the halides such as chloride, bromide and iodide.

The acid addition salts according to the invention may in principle be derived from any pharmaceutically acceptable, suitable organic or inorganic acid known to those in the art. Preferably the acid itself is water-soluble. Examples of suitable inorganic acids are hydrochloric acid, hydrobromic acid, hydroiodic acid, nitric acid, sulphuric acid and phosphoric acid; examples of suitable organic acids are lower aliphatic mono-, di- or tri-carboxylic acids, such as acetic acid, propionic acid, butyric acid, caproic acid, malonic acid, succinic acid, glutaric acid, maleic acid, fumaric acid, tartaric acid, malic acid, pyruvic acid, lactic acid and citric acid.

The acid addition salts of the invention are prepared in the usual manner known to those in the art by adding the acid in question to the 16-mono-quaternary ammonium derivative according to formula I in a suitable liquid.

A relatively stable, injectable, aqueous pharmaceutical preparation or composition of the 16-mono-quaternary ammonium derivative according to formula (I) can thus be obtained by dissolving the acid addition salt of the invention in water under aseptic conditions. It can also be obtained by combining a pharmaceutically acceptable acid with an aqueous solution of the 16-mono-quaternary ammonium derivative according to formula I under aseptic conditions, whereby the acid addition salt is formed in situ.

The pharmaceutical composition may further be stabilized, if desired, by the addition of a pharmaceutically acceptable buffer system, which buffers are generally in the range of about pH 3 to about pH 4.5, such as an acetic acid/sodium acetate buffer or a citric acid/sodium phosphate buffer. Where the acid addition salt used or prepared in situ, is the acetate or citrate, the quantity of acetic acid or citric acid in the buffer system may obviously be reduced or omitted, dependent on the concentration of the acid addition salt in the aqueous solution.

The aqueous pharmaceutical preparation may be administered directly, may be stored for some time, or may be lyophilised.

The new acid addition salts of the invention are administered in the same molar quantities or dosages as is known or described for the known 2,16-bis-quaternary ammonium derivatives of 2β,16β-dipiperidino-3α,17-dihydroxy-5α-androstane 3α,17β-diesters.

Although the invention has been described with respect to the specific embodiments above, numerous variations and modifications will become evident to those skilled in the art without departing from the scope and spirit of the invention as described above, defined in the appended claims, and as shown in the following Examples.

EXAMPLE I

2β,16β-dipiperidino-5α-androstane-3α,17β-diol diacetate 16βN—methobromide hydrochloride A saturated solution of hydrogen chloride in dry ether (10 ml) was added dropwise to a stirred, cooled solution of 2β,16β-dipiperidino-5α-androstane-3α,17β-diol diacetate 16βN-methobromide (0.5 g) in dry methylene dichloride (10 ml), and the resulting solution evaporated to dryness in vacuo. The product was crystallised from acetone to afford 2β,16β-di-piperidino-5α-androstane-3α,17β-diol diacetate 16βN-methobromide hydrochloride as a white solid (0.39 g) m.p. 208°–212°.

2β,16β-dipiperidino-5α-androstane-3α,17β-diol 3α-propionate 17β-acetate 16βN-methobromide hydrochloride was similarly prepared and crystallised from acetone, m.p. 213°–222°.

In a similar manner may be prepared:
2β,16β-dipiperidino-5α-androstane-3α-ol 3α-acetate 16βN-methobromide hydrochloride;
2β,16β-dipiperidino-5α-androstane-3α-ol 3α-acetate 16βN-allylobromide hydrochloride; and
2β,16β-dipiperidino-5α-androstane-3α-ol 3α-acetate 16βN-propargylobromide hydrochloride.

EXAMPLE II

Hydrobromide

A solution of hydrogen bromide (1.5 mol) in dry ether (0.66 ml) was added to a stirred, cooled solution of 2β,16β-dipiperidino-5α-androstane-3α-17β-diol diacetate 16βN-methobromide (0.5 g) in dry methylene dichloride (10.0 ml), and the resulting solution evaporated to dryness in vacuo to yield a pale yellow solid (0.58 g). The product was refluxed in acetone for 15 min., cooled, then filtered and dried to afford 2β,16β-dipiperidino-5α-androstane-3α,17β-diol diacetate 16βN-methobromide hydrobromide as an off-white solid (0.35 g), m.p. 226°–238° (decomp.).

2β,16β-dipiperidino-5α-androstane-3α,17β-diol 3α-butyrate 17β-acetate 16βN-methobromide hydrobromide was similarly prepared and crystallised from acetone, m.p. 216°–220°.

EXAMPLE III

Maleate

A solution of maleic acid (0.085 g, 1.0 mol) in acetone (5 ml) was added with stirring to a solution of 2β,16β-dipiperidino-5α-androstane-3α,17β-diol diacetate 16βN-methobromide (0.5 g) in dry methylene dichloride (10 ml), and the resulting mixture evaporated to dryness in vacuo. The product was slaked with ether, filtered and dried to afford 2β,16β-dipiperidino-5α-androstane-3α,17β-diol diacetate 16βN-methobromide maleate as a pale yellow solid (0.55 g), m.p. 139°–145°.

2β,16β-dipiperidino-5α-androstane-3α,17β-diol 3α-butyrate 17β-acetate 16βN-methobromide maleate was similarly prepared and crystallised from acetone, m.p. 208°–217°.

EXAMPLE IV

Citrate

A solution of citric acid (0.16 g, 1.0 mol) in acetone (5 ml) was added with stirring to a solution of 2β,16β-dipiperidino-5α-androstane-3α,17β-diol diacetate 16βN-methobromide (0.5 g) in dry methylene dichloride (10 ml) and the resulting mixture evaporated to dryness in vacuo. The product was slaked with ether, filtered and dried to afford 2β,16β-dipiperidino-5α-androstane-3α,17β-diol diacetate 16βN-methobromide citrate as a white solid (0.59 g), m.p. 130°–158°.

2β,16β-dipiperidino-5α-androstane-3α,17β-diol 3α-propionate 17β-acetate 16βN-methobromide citrate was similarly prepared as an off white solid, m.p. 138°–173°.

EXAMPLE V

Phosphate

A solution of ortho phosphoric acid (0,075 g, 1.0 mol) in dry ether (10 ml) was added with stirring to a solution of 2β,16β-dipiperidino-5α-androstane-3α,17β-diol diacetate 16βN-methobromide (0.5 g) in dry methylene dichloride (10 ml) and the resulting mixture evaporated to dryness in vacuo. The product was slaked with ether, filtered and dried to afford 2β,16β-dipiperidino-5α-androstane-3α,17β-diol diacetate 16βN-methobromide phosphate as a white solid (0.58 g), m.p. 206°–223°.

2β,16β-dipiperidino-5α-androstane-3α,17β-diol 3α-pivalate 17β-acetate 16βN-methobromide phosphate was similarly prepared as a white solid, m.p. 198°–207°.

EXAMPLE VI

2β,16β-dipiperidino-5α-androstane-3α,17β-diol 3α-pivalate 17β-acetate 16βN-methobromide tartrate A solution of tartaric acid (0.108 g, 1.0 mol) in acetone (8 ml) was added with stirring to a solution of 2β,16β-dipiperidino-5α-androstane-3α,17β-diol 3α-pivalate 17β-acetate 16βN-methobromide (0.5 g) in dry methylene dichloride (10 ml) and the resulting mixture evaporated to dryness in vacuo. The product was slaked with ether, filtered and dried to afford 2β,16β-dipiperidino-5α-androstane-3α,17β-diol 3α-pivalate 17β-acetate 16βN-methobromide tartrate as a white solid (0.59 g), m.p. 163°–212°.

EXAMPLE VII

Stability in Water

Aqueous solutions of 10 mg/ml of

Compound "A": 2β,16β-dipiperidino-5α-androstane-3α,17β-diol diacetate 16βN-methobromide known to those in the art, and Compound "B": 2β,16β-piperidino-5α-androstane-3α,17β-diol diacetate 16βN-methobromide hydrochloride of the invention were prepared and kept at room temperature.

Samples (20 μg) were taken at intervals, spotted directly onto TLC plates and run against a freshly prepared solution of A. The TLC solvent systems used were:

(i) n-butanol:water (6:1) on Macherey-Nagel precoated ALOX 25 ® plates, and (ii) methanol:IM sodium acetate (1:1) on Merck & Co., Inc., (P.O. Box 2000, Rahway, N.J. 07065) Silica Gel 60 ® plates

| Day | Presence of "A" in The Solution | Presence of "B" in The Solution |
|---|---|---|
| 0 | 100 | 100 |
| 1 | 10 | 98–99 |
| 2 | 5–10 | 98–99 |
| 4 | 5–10 | 95–97 |
| 8 | 3–8 | 94–96 |
| 28 | not detectable | 92–94 |
| 43 | not detectable | 80–90 |

Aqueous solutions of 15 mg/ml were further prepared of:

the hydrochloride, hydrobromide, maleate, citrate and phosphate of 2β,16β-dipiperidino-5α-androstane-3α,17β-diol diacetate-16βN-methobromide;

the hydrochloride and citrate of 2β,16β-dipiperidino-5α-androstane-3α,17β-diol 3α-propionate 17β-acetate 16βN-methobromide;

the hydrobromide and maleate of 2β,16β-dipiperidino-5α-androstane-3α,17β-diol 3α-butyrate 17β-acetate 16βN-methobromide; and the phosphate and tartrate of 2β,16β-dipiperidino-5α-androstane-3α,17β-diol 3α-pivalate 17β-acetate 16βN-methobromide; and examined by thin layer chromatography (TLC) over a period of 8 days. (System:methanol:sodium acetate IM 1:1 on Merck Silica Gel 60 ® plates). Both hydrochlorides showed a decomposition of approximately 5%, the other salts less than 5%. In the same period a 10 mg/ml solution of "A" showed a decomposition of about 92–97%.

EXAMPLE VIII

Stability in plasma

Blank dog plasma solutions of 0.2 g/ml of

Compound "A": 2β,16β-dipiperidino-5α-androstane-3α,17β-diol diacetate 16βN-methobromide known to those in the art, and Compound "B": 2β,16β-piperidino-5α-androstane-3α,17β-diol diacetate 16βN-methobromide hydrochloride of the invention were prepared and kept at room temperature.

Samples (one ml) were taken at intervals (i.e. after 1.5 h, 4 h and 24 h) and processed as follows:

One ml portion of plasma was mixed with 1 ml phosphate buffer (pH=6.5) and 100 μl of picric acid (0.05 M, pH=6.5, adjusted with NaOH). Compound "A" or "B" and its possible hydrolysis products were extracted as ion pairs to a methylene chloride phase (2 ml) by gently shaking. The methylene chloride phase was evaporated to dryness under nitrogen at 40° C. The residue was redissolved in 50 μl MeOH/CH$_3$CN (1:1, v/v). An aliquot was injected into a HPLC system, employing a straight phase Lichrosorb Si 60 column (L=25 cm, i.d.=4.0 mm, d$_p$=10 μm) thermostatted with a water jacket at 45° C. The solvent consisted of MeOH, 0.05 M NH$_4$Cl and 1% NH$_4$OH, which was shaken ultrasonically before use during 30 minutes, the flow rate was 1 ml/min and the compounds were monitored by means of UV detection at 215 nm.

Results:

| Time (h) | Percentage of "A" in plasma | Percentage of "B" in plasma |
|---|---|---|
| 0 | 100 | 100 |
| 1.5 | 72 | 100 |
| 4 | 51 | 100 |
| 24 | 7 | 100 |

It is claimed as the invention:

1. A pharmaceutically acceptable acid addition salt of the 16β-mono-quaternary ammonium derivative of either a 3α,17β-di-lower aliphatic ester of 2β,16β-dipiperidino-3α,17β-dihydroxy-5α-androstane or a 3α-lower aliphatic ester of 2β,16β-dipiperidino-3α-hydroxy-5α-androstane.

2. Acid addition salt according to claim 1 of a compound of the general formula:

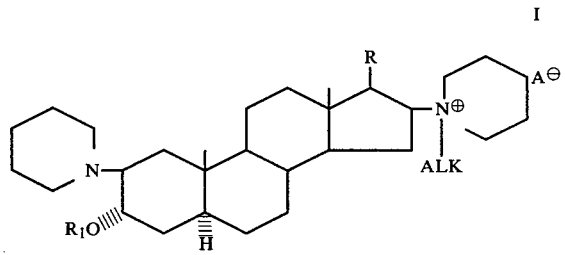

wherein:

(a) R represents hydrogen or the moiety —OR$_2$;

(b) R$_1$ and R$_2$ each represent an unsubstituted acyl group derived from a lower aliphatic carboxylic acid of one to about six carbons;

(c) ALK is an alkyl, alkenyl or alkynyl group of one to about four carbon atoms; and (d) A$^\ominus$ represents a pharmaceutically acceptable organic or inorganic anion.

3. The acid addition salt of a compound of claim 2 wherein at least one of R$_1$ and R$_2$ is acetyl.

4. The acid addition salt of a compound of claim 2 wherein A$^\ominus$ is selected from the group consisting of methyl-sulfate, p-toluene sulfonate, chloride, bromide and iodide.

5. The acid addition salt of a compound of claim 2 wherein ALK is methyl.

6. The acid addition salt of a compound of claim 1 wherein the salt is derived from one of the acids selected from the group consisting of hydrochloric acid, hydrobromic acid, hydroiodic acid, nitric acid, sulphuric acid, phosphoric acid, acetic acid, propronic acid, butyric acid, caproic acid, malonic acid, succinic acid, glutaric acid, maleic acid, fumaric acid, tartaric acid, malic acid, pyruvic acid, lactic acid, and citric acid.

7. 2β,16β-dipiperidino-5α-androstane-3α,17β-diol diacetate 16βN-methobromide hydrochloride.

8. 2β,16β-dipiperidino-5α-androstane-3α,17β-diol 3α-proprionate 17β-acetate 16βN-methobromide hydrochloride.

9. 2β,16β-dipiperdino-5α-androstane-3α-ol 3α-acetate 16βN-methobromide hydrochloride.

10. 2β,16β-dipiperidino-5α-androstane-3α-ol 3α-acetate 16βN-allylobromide hydrochloride.

11. 2β,16β-dipiperidino-5α-androstane-3α-ol 3α-acetate 16βN-propargylobromide hydrochloride.

12. 2β,16β-dipiperidino-5α-androstane 3α,17β-diol diacetate 16βN-methobromide hydrobromide.

13. 2β,16β-dipiperidino-5α-androstane-3α,17β-diol 3α-butyrate 17β-acetate 16βN-methobromide hydrobromide.

14. 2β,16β-dipiperidino-5α-androstane-3α,17β-diol diacetate 16βN-methobromide maleate.

15. 2β,16β-dipiperidino-5α-androstane-3α,17β-diol, 3α-butyrate 17β-acetate 16βN-methobromide maleate.

16. 2β,16β-dipiperidino-5α-androstane-3α,17β-diol diacetate 16βN-methobromide citrate.

17. 2β,16β-dipiperidino-5α-androstane-3α,17β-diol 3α-propionate 17β-acetate 16βN-methobromide citrate.

18. 2β,16β-dipiperidino-5α-androstane-3α,17β-diol diacetate 16βN-methobromide phosphate.

19. 2β,16β-dipiperidino-5α-androstane-3α,17β-diol 3α pivalate 17β-acetate 16βN-methobromide phosphate.

20. 2β,16β-dipiperidino-5α-androstane-3α,17β-diol 3α pivalate 17β-acetate 16βN-methobromide tartrate.

21. A pharmaceutical composition useful as a neuromuscular blocking agent, comprising:
   (A) a pharmaceutically effective amount of a pharmaceutically acceptable acid addition salt of the 16β-mono-quaternary ammonium derivative of either a 3α,17β-di-lower aliphatic ester of a 3α-lower aliphatic ester of 2β,16β-dipiperidino-3α-hydroxy-5α-androstane; and
   (B) water,
whereby the acid addition salt is formed in situ.

22. The composition of claim 21, wherein a pharmaceutically acceptable buffer system is added to buffer the composition in the range of from about pH 3 to about pH 4.5.

23. The composition of claim 21 or 22, wherein a pharmaceutically acceptable amount of an acid addition salt of 2β,16β-dipiperidino-3α,17β-dihydroxy-5α-androstane 3α,17β-diacetate 16β-methobromide is present.

24. The composition of claim 21, wherein the acid addition salt is of a compound of the formula:

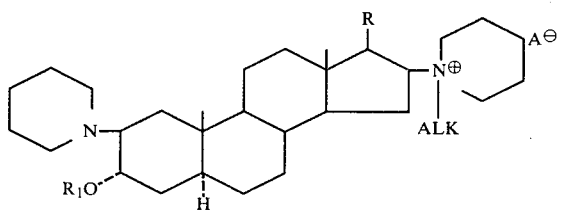

wherein:
(a) R represents hydrogen or the moiety —OR₂;

(b) R₁ and R₂ each represent an unsubstituted acyl group derived from a lower aliphatic carboxylic acid of one to about six carbons;
(c) ALK is an alkyl, alkenyl, or alkynyl group of one to about four carbon atoms; and
(d) A⊖ represents a pharmaceutically acceptable organic or inorganic anion;
is present.

25. Acid addition salt according to claim 1 having the general formula:

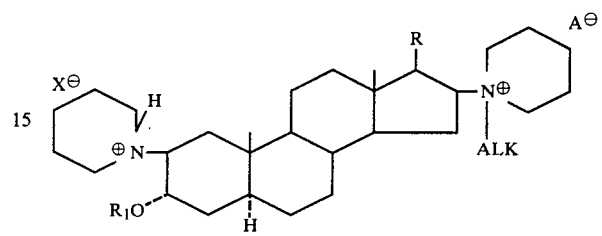

wherein:
(a) R represents hydrogen or the moiety —OR₂;
(b) R₁ and R₂ each represent an unsubstituted acyl group derived from a lower aliphatic carboxylic acid of one to about six carbons;
(c) ALK is an alkyl, alkenyl or alkynyl group of one to about four carbon atoms; and
(d) A⊖ and X⊖ each represents a pharmaceutically acceptable organic or inorganic anion.

26. The salt of claim 25 where X⊖ is the same anion as A⊖.

27. A pharmaceutical composition useful as a neuromuscular blocking agent comprising
   (a) a neuromuscular blocking effective amount of a pharmaceutically acceptable acid addition salt of the 16β-monoquaternary ammonium derivative of either a 3α,17β-di-lower aliphatic ester or a 3α-lower aliphatic ester of 2β,16β-dipiperidino-3α-hydroxy-5α-androstane, and
   (b) water.

28. The composition of claim 27 further comprising a pharmaceutically acceptable buffer system to buffer the composition to a pH ranging from about 3 to about 4.5.

29. The composition of claim 27 or 28 wherein said acid addition salt is an acid addition salt of 2β,16β-dipiperidino-3α,17β-dihydroxy-5α-androstane 3α,17β-diacetate 16β-methobromide.

30. The composition of claim 27 wherein said acid addition salt is of a compound of the formula:

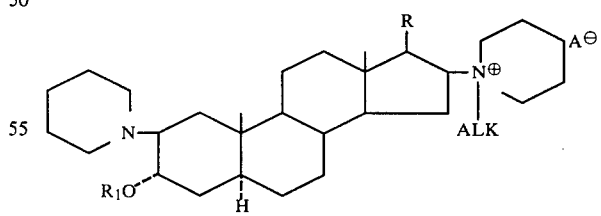

wherein:
(a) R is hydrogen or the moiety —OR₂;
(b) R₁ and R₂ each represent an unsubstituted acyl group derived from a lower aliphatic carboxylic acid of one to about six carbons;
(c) ALK is an alkyl, alkenyl, or alkynyl group of one to about four carbon atoms; and
(d) A⊖ represents a pharmaceutically acceptable organic or inorganic anion.

* * * * *

UNITED STATES PATENT OFFICE
CERTIFICATE OF CORRECTION

Patent No. 4,237,126          Dated  December 2, 1980

Inventor(s) Ian C. Carlyle; Thomas Sleigh; David S. Savage

It is certified that error appears in the above-identified patent and that said Letters Patent are hereby corrected as shown below:

On the front page of the patent (disclosing the inventor, assignee, Abstract, etc.) under the heading "References Cited", and subheading "Other Publications", correct the citation of Buckett et al to read --W. R. Buckett, C. L. Hewett, and D. S. Savage, "Pancuronium Bromide and Other Steroidal Nueromuscular Blocking Agents Containing Acetylcholine Fragments", J. MEDICINAL CHEM. $\underline{16}$(10) at 1116-1123 (1973).--

In col. 1, line 21, after "chemistry", underline "$\underline{16}$".

In col. 1, line 28, before "-Mono", underline "$\underline{16}$".

In col. 3, line 5, at the end of the line, delete "-".

In col. 3, line 28, underline "Example I".

In col. 3, lines 29-30, under "Example I", underline "$2\beta$, $16\beta$-dipiperidino-$5\alpha$-androstane-$3\alpha$, $17\beta$-diol diacetate $16\beta$N-methobromide hydrochloride."

In col. 3, line 53, underline "Example II".

In col. 3, line 54, under "Example II", underline "Hydrobromide".

In col. 4, line 4, underline "Example III".

In col. 4, line 5, under Example III, underline "Maleate".

In col. 4, line 21, underline "Example IV".

In col. 4, line 23, under "Example IV", underline "citrate".

In col. 4, line 38, underline "Example V".

In col. 4, line 40, under "Example V", underline "Phosphate".

In col. 4, line 41, change "0,075" to --0.075--.

UNITED STATES PATENT AND TRADEMARK OFFICE
CERTIFICATE OF CORRECTION

PATENT NO. : 4,237,126                    Page 2 of 3
DATED     : December 2, 1980
INVENTOR(S) : Ian C. Carlyle et al.

It is certified that error appears in the above—identified patent and that said Letters Patent is hereby corrected as shown below:

In col. 4, line 54, underline "Example IV".

In col. 4, line 55, under Example VI, underline "2β, 16β-dipiperidino-5α-androstane-3α, 17β-diol 3α-pivalate 17β-acetate 16βN-methobromide tartrate."

In col. 5, line 1, underline "Example VII".

In col. 5, line 2, under "Example VII", underline "Stability in Water".

In col. 5, line 19, change the zero "0" after "P" to letter --O--.

UNITED STATES PATENT AND TRADEMARK OFFICE
CERTIFICATE OF CORRECTION

PATENT NO. : 4,237,126
DATED : December 2, 1980
INVENTOR(S) : Ian C. Carlyle et al.

It is certified that error appears in the above—identified patent and that said Letters Patent is hereby corrected as shown below:

In col. 5, line 52, underline "Example VIII".

In col. 5, line 54, under "Example VIII", underline "Stability in Plasma".

In col. 6, line 14, underline "Results".

In col. 6, line 23, put in all capital letters and underline "IT IS CLAIMED AS THE INVENTION:"

In col. 8, under Claim 25, correct the formula to

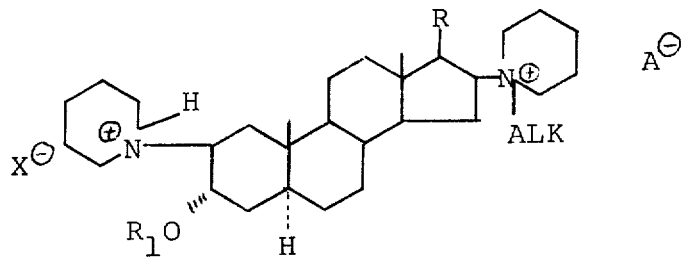

Signed and Sealed this

Tenth Day of March 1981

[SEAL]

Attest:

RENE D. TEGTMEYER

Attesting Officer    Acting Commissioner of Patents and Trademarks